United States Patent
Delius et al.

(10) Patent No.: US 10,371,655 B2
(45) Date of Patent: Aug. 6, 2019

(54) SYSTEM FOR A PAVER FOR DETERMINING A COOLING BEHAVIOR

(71) Applicant: JOSEPH VOEGELE AG, Ludwigshafen/Rhein (DE)

(72) Inventors: Henning Delius, Hanhofen (DE); Arnold Rutz, Ludwigshafen (DE); Martin Buschmann, Neustadt (DE)

(73) Assignee: JOSEPH VOEGELE AG, Ludwigshafen/Rhein (DE)

( * ) Notice: Subject to any disclaimer, the term of this patent is extended or adjusted under 35 U.S.C. 154(b) by 63 days.

(21) Appl. No.: 14/836,274

(22) Filed: Aug. 26, 2015

(65) Prior Publication Data

US 2016/0061755 A1 Mar. 3, 2016

(30) Foreign Application Priority Data

Aug. 27, 2014 (EP) ..................... 14182526

(51) Int. Cl.
*G01N 25/20* (2006.01)
*G01N 25/00* (2006.01)
(Continued)

(52) U.S. Cl.
CPC ............. *G01N 25/00* (2013.01); *E01C 19/42* (2013.01); *E01C 19/48* (2013.01); *E01C 23/01* (2013.01);
(Continued)

(58) Field of Classification Search
None
See application file for complete search history.

(56) References Cited

U.S. PATENT DOCUMENTS

| 4,910,593 A | 3/1990 | Weil |
| 5,362,176 A | 11/1994 | Sovik |

(Continued)

FOREIGN PATENT DOCUMENTS

| CN | 102182137 A | 9/2011 |
| CN | 102691251 A | 9/2012 |

(Continued)

OTHER PUBLICATIONS

A real-time system for prediction cooling within the asphalt layer to support rolling operations Alexandr Vasenev, Frank Bijleveld, Timo Hartmann, André G. Dorée; 5th Eurasphalt & Eurobitume Congress, Jun. 13-15, 2012, Istanb (Year: 2012).*

(Continued)

*Primary Examiner* — Erica S Lin
(74) *Attorney, Agent, or Firm* — Brooks Kushman P.C.

(57) ABSTRACT

A system comprising a temperature measurement device for repeatedly detecting temperature values of a pavement laid by a paver. The system is configured for ascertaining a temperature value for a specific measuring point at at least two different moments in time by means of the temperature measurement device, the specific measuring point lying in an area of the laid pavement. The system additionally comprises an evaluation unit, the evaluation unit being configured for determining a cooling behavior of the laid pavement. This is done by making use of the at least two different temperature values that have been detected for the specific measuring point at the at least two different moments in time.

19 Claims, 9 Drawing Sheets

(51) Int. Cl.
  *E01C 19/42* (2006.01)
  *E01C 19/48* (2006.01)
  *G01J 5/00* (2006.01)
  *G01N 33/42* (2006.01)
  *E01C 23/01* (2006.01)

(52) U.S. Cl.
  CPC ............ *G01J 5/0022* (2013.01); *G01N 33/42* (2013.01); *G01J 2005/0077* (2013.01)

(56) References Cited

U.S. PATENT DOCUMENTS

| | | | |
|---|---|---|---|
| 6,112,903 | A | 9/2000 | Kimmel et al. |
| 6,227,762 | B1 * | 5/2001 | Van Velsor ............. E01C 19/48 404/77 |
| 6,749,364 | B1 * | 6/2004 | Baker ................... E01C 19/288 404/118 |
| 7,873,492 | B2 | 1/2011 | Ackermann |
| 8,099,218 | B2 | 1/2012 | Glee et al. |
| 9,255,364 | B2 | 2/2016 | Ichikawa |
| 9,447,549 | B2 | 9/2016 | Buschmann et al. |
| 2002/0175691 | A1 * | 11/2002 | Sovik ....................... G01N 9/00 324/654 |
| 2004/0264542 | A1 | 12/2004 | Kienitz |
| 2009/0142133 | A1 * | 6/2009 | Glee ...................... E01C 19/004 404/75 |
| 2009/0317186 | A1 | 12/2009 | Glee et al. |
| 2012/0218411 | A1 | 8/2012 | Wu et al. |
| 2012/0263532 | A1 | 10/2012 | Rutz et al. |
| 2014/0086684 | A1 | 3/2014 | Sehr et al. |
| 2014/0347448 | A1 | 11/2014 | Hegemann et al. |
| 2015/0199576 | A1 | 7/2015 | Ichikawa |
| 2016/0042235 | A1 | 2/2016 | Buschmann et al. |
| 2016/0350907 | A1 | 12/2016 | Simula et al. |

FOREIGN PATENT DOCUMENTS

| | | |
|---|---|---|
| CN | 103292930 A | 9/2013 |
| CN | 104101434 A | 10/2014 |
| DE | 102008058481 A1 | 7/2009 |
| EP | 2 634 747 A1 | 9/2013 |
| EP | 2666908 A1 | 11/2013 |
| JP | 2-293685 A | 12/1990 |
| JP | 4-77608 U | 7/1992 |
| JP | 06228911 A | 8/1994 |
| JP | 7-42370 U | 8/1995 |
| JP | 2000-258584 A | 9/2000 |
| JP | 2005-94958 A | 4/2005 |
| JP | 2005097958 A | 4/2005 |
| JP | 2008268217 A | 11/2008 |
| WO | 0070150 A1 | 11/2000 |
| WO | 2004034351 A2 | 4/2004 |

OTHER PUBLICATIONS

European Communication dated Apr. 18, 2016, Application No. 14 182 526.5-1604, Applicant Joseph Vögele AG, 6 Pages.
English Translation of Japanese Office Action dated Sep. 6, 2016, Application No. 2015-157259, Dispatch No. 398496, 3 pages.
Extended European Search Report dated Feb. 9, 2015, Application No. 14182526.5-1604, Applicant Joseph Voegele AG, 6 Pages.
Chinese Search Report dated Jan. 15, 2018, Application No. 2015105323403, 2 Pages.
Chinese Office Action dated Feb. 1, 2018, Application No. 201510532340.3, Applicant Joseph Voegele AG, 7 Pages.
U.S. Non-Final Office Action dated Aug. 2, 2017, U.S. Appl. No. 14/817,823, 48 Pages.
U.S. Final Office Action dated Feb. 22, 2018, U.S. Appl. No. 14/817,823, 32 Pages.
Extended European Search Report dated Jan. 30, 2015, U.S. Appl. No. 14/798,116—1562, Applicant Joseph Voegele AG, 8 Pages.
European Communication dated May 11, 2015, Application No. 14 179 811.6-1562, Applicant Joseph Voegele AG, 4 Pages.
Extended European Search Report dated Sep. 9, 2016, Application No. 14 179 811.6-1562, Applicant Joseph Voegele AG, 5 Pages.
Japanese Office Action dated Jun. 28, 2016, Application No. 2015-148419, 4 Pages.
Indian Examination Report dated Feb. 23, 2018, Application No. 2255/DEL/2015, Applicant Joseph Voegele AG, 5 Pages.
U.S. Office Action dated Aug. 10, 2018, U.S. Appl. No. 14/817,823, 51 Pages.
Indian Examination Report dated Mar. 13, 2019, Application No. 2434/DEL/2015, 7 Pages.
U.S. Notice of Allowance dated Feb. 13, 2019, U.S. Appl. No. 14/817,823, 16 Pages.

* cited by examiner

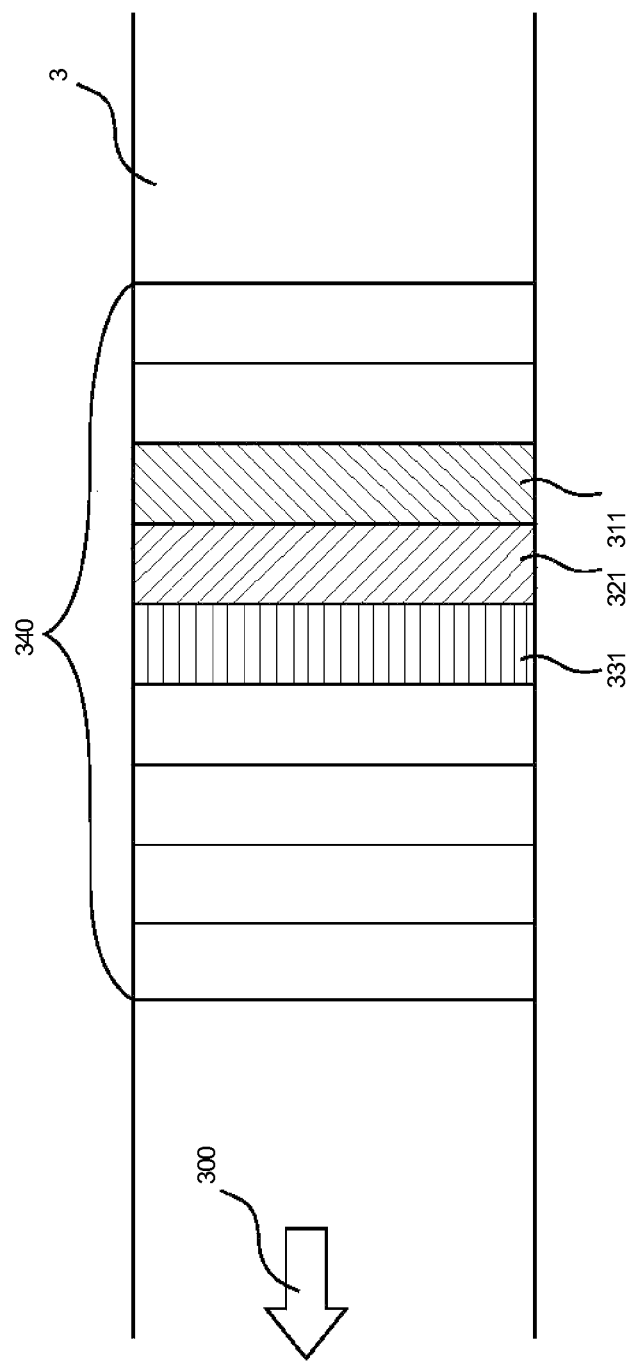

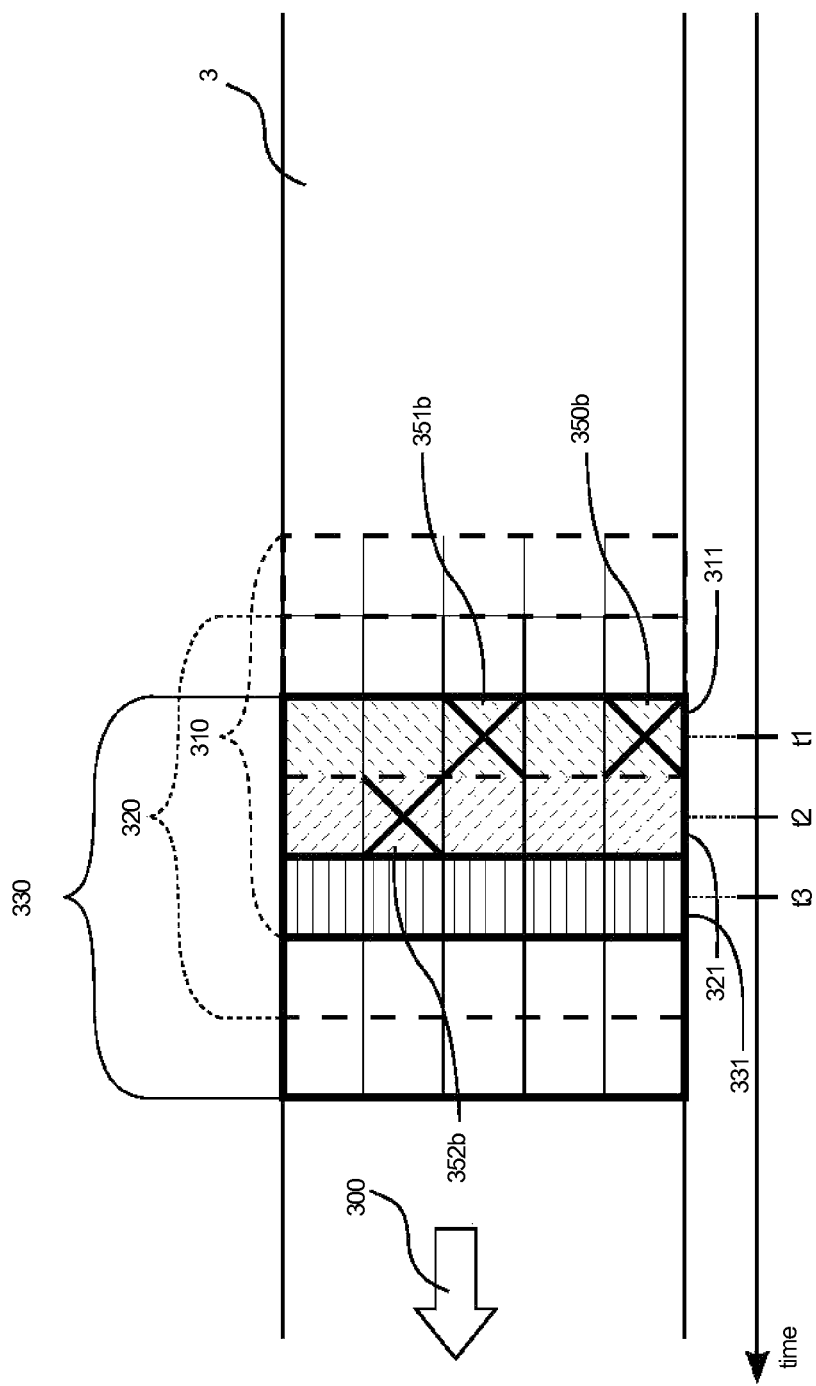

SYSTEM FOR A PAVER FOR DETERMINING A COOLING BEHAVIOR

CROSS-REFERENCE TO RELATED APPLICATIONS

This application claims foreign priority benefits under 35 U.S.C. § 119(a)-(d) to European patent application number EP 14 182 526.5, filed Aug. 27, 2014, which is incorporated by reference in its entirety.

TECHNICAL FIELD

The present disclosure relates to a system comprising a temperature measurement device for continuously or repeatedly detecting temperature values of a pavement laid by means of a paver, and in particular to such a system for determining or documenting the laying temperature and the cooling behavior of the laid pavement.

BACKGROUND

A paver is a machine by means of which unbound and bound layers or pavements can be produced. As soon as a laid pavement is made available for its intended use, subsequent improvements entail substantial efforts, such as the closure of road sections or parts of buildings. Hence, quality control is of great importance in the field of asphalt laying. A system which allows the quality of asphalt laying or the quality of the laid asphalt to be measured is shown in WO 2004/034351 A2. In particular, it is possible to manually check the properties of the asphalt, and, in so doing, individual measurement processes can be linked with site data.

An important process variable in road construction is, in particular, the processing temperature of the pavements laid, such as asphalt or bitumen. The processing temperature substantially influences the usage properties, such as stability, layer adhesion and service life of the laid pavements. Pavers typically distribute the paving material and carry out precompacting of a surface of the paving material with a screed, which is attached to the rear end of the paver and is drawn thereby. The thus laid pavement is subsequently compacted still further by rollers. Like other factors, such as environmental and weather conditions during laying, the temperature of the material in different stages of the laying process influences the efficiency and the success of a paving job.

Processing e.g., paving material under optimum temperature conditions has long been recognized as important, but such processing often entails manual control measurements on the part of the support and operating staff. Paving material is typically obtained at a comparatively high temperature at an asphalt or bitumen plant. Depending on the distance a supply machine has to travel so as to reach a work site as well as on the traffic and the ambient temperature, the asphalt may cool to a certain extent prior to delivery. In addition, progress of the paving machines and of the compacting machines or rollers may vary. The extent of cooling, once the paving material has finally reached the paving machine or paver, may vary depending on the temperature of the paving material at delivery, environmental factors, etc. In some cases, paving material may segregate within the paving machine, and thus relatively cooler and relatively hotter pockets or accumulations of material within the machine may exist, leading to unexpected, mostly punctual, temperature gradients in the paving material once the latter is distributed on the work surface. In a typical laying process, the paving material is discharged, distributed by the paving machine or paver, and subsequently precompacted by means of the screed, and is then ready to be compacted still further by the various compacting machines. In the course of this process, the material temperature can deviate significantly from an expected temperature. In addition, the material temperature may be non-uniform from one paved region to the next due to changing weather conditions or due to unintended segregation or poor mixing.

Due to the importance of the laying temperature of the pavement in the laying process, measuring of the laying temperature becomes increasingly important and, within the last few years, various solutions have been developed, which satisfy the demand for metrological proof of the laying temperature and thus facilitate also subsequent improvements. Known systems measure for this purpose the laying temperature behind the paver, in particular behind the screed. The systems available range from a pyrometer array to thermal or infrared scanners and also to pivotable pyrometers. These systems are used for obtaining a more or less areal impression of the temperature profile behind the paver.

Other systems for obtaining laying temperature information are based on data obtained from an infrared camera whose image data are arithmetically converted into scanning lines by means of a suitable software. These lines of an ascertained thermal image show the temperature profile at a certain distance from the paver or the trailing edge of the screed. Each line may here represent the temperature profile of the paved layer transversal to the travelling direction of the paver after the individual lines have been combined so as to form a planar image, a so-called temperature map or two-dimensional temperature profile. These images can subsequently be used for assessing the temperature distribution of the laid asphalt. As mentioned above, a temperature distribution having the highest possible uniformity is here a quality characteristic, since this will provide uniform preconditions for subsequent compacting by means of rollers.

WO 00/70150 A1 discloses a temperature monitoring system of the type in question, which is secured in position on a paver and which scans the temperature of the laid pavement line by line. The temperature data obtained are either directly used for controlling the screed or communicated to other machines of the paving train in the laying process.

DE 10 2008 058 481 A1 describes an evaluation of such a temperature profile during the paving process. In particular, the adaptation of a paving process to the individual machines of the paving train is described. Especially on the basis of the obtained temperature information of the laid asphalt, the distance between the compacting rollers and the paving machine or paver is adapted such that the asphalt will not be processed by the subsequent compacting rollers within a temperature range referred to as "tender zone." To this end, a comparison between predicted temperatures and actually measured temperatures is suggested. If there is a difference between the predicted temperature and the actually measured temperature, the machines are decelerated or accelerated accordingly. For predicting the temperature, a model is used, which makes use of the external weather conditions, such as the ambient temperature. If the model predicts comparatively slow cooling due to high ambient temperatures, the machines can travel at a comparatively lower speed or such that the distance between them is enlarged in a suitable manner.

The temperature measurements of the known methods for monitoring the laying process do, however, not permit any direct conclusions with respect to the actual cooling behavior of the laid pavement. In the case of the known measurement systems making use of pointwise or line-by-line scanning, it is attempted to simulate the cooling behavior by models. The models take into account external factors, such as the weather. Hence, these solutions require additional sensors, e.g., wind gauges or rain gauges, and the user has to manually enter into the system the cloudiness at the time in question. For improving the quality of the measurement results and for simplifying the method, it is therefore desirable to be able to do without such additional sensors and manual inputs.

A direct measurement or determination of the cooling behavior of the laid pavement is, however, not possible by means of the known system. Even systems in which the laying temperature is continuously detected so as to obtain an areal temperature image of the laid pavement, it is impossible to draw conclusions with respect to the cooling behavior or the cooling rate of the laid pavement, since the lines of the thermal image were recorded during a continuous laying process at the same moment in time and at the same distance from the screed.

SUMMARY

It is therefore an object of the present disclosure to provide an improved system for detecting, by means of a temperature measurement device, temperature values of a pavement laid by a paver, said system allowing in particular an improvement of the measurement result and reducing the number of sensors required or the number of parameters that have to be manually entered.

This object is achieved by a system according to the present disclosure. A paver according to the present disclosure and a method according to the present disclosure as well as a computer-readable storage medium with instructions of a corresponding control method according to the present disclosure are also provided. Improved further developments of the disclosure are defined by the additional features of the subclaims.

The disclosure relates in particular to a system comprising a temperature measurement device for repeatedly detecting temperature values of a pavement laid by a paver. The system is here configured for detecting a temperature value for a specific measuring point in the area of the laid pavement at at least two different moments in time by means of the temperature measurement device. The system additionally comprises an evaluation unit, said evaluation unit being configured for determining a cooling behavior of the laid pavement. In so doing, it makes use of the at least two different temperature values that have been detected for the specific measuring point at the at least two different moments in time.

The respective time interval between the at least two different moments in time may here be predetermined. This enables the evaluation unit to determine or predict the cooling behavior of the laid pavement making use of the then known time interval between the at least two different moments in time and the at least two detected temperature values for the specific measuring point.

The temperature values detected are preferably temperature values of the laid pavement, which are detected by the temperature measurement device during or after precompacting by means of a screed of the paver. For this case, the temperature measurement device may be configured such that it detects temperature values at a respective predetermined or easily ascertainable distance to the paver or the screed. The exact position of the measuring points can thus be determined or recognized more easily. For example, a specific measuring point can be ascertained or recognized on the basis of its respective distance to the paver or the screed at the at least two different moments in time during the laying process. Since the distance in time between the measurements as well as the distance in space between the measurements are known or can be ascertained, the detected data can be used for representing the temperature over time and for ascertaining thus also a measure for the cooling or the cooling rate of the pavement surface.

According to a further embodiment of the present disclosure, the temperature measurement device is configured such that it will be able to detect, at each time of measurement, a plurality of temperature values in a two-dimensional area on the surface of the laid pavement. This two-dimensional area is also referred to as detection area of the temperature measurement device. Hence, the at least two different moments in time, at which the temperature measurement device carries out temperature measurements, correspond to at least two different two-dimensional detection areas. These two-dimensional areas are chosen such that they overlap. In addition, the specific measuring point is chosen such that it lies in the overlapping region of the at least two detection areas. In this way it is achieved that, for the specific measuring point on the laid pavement, multiple temperature measurements are carried out at different moments in time, without the necessity of executing any additional measurements.

According to a further embodiment, the temperature values are detected line-by-line by means of the temperature measurement device, so that each detected line represents a temperature profile of the laid pavement transversal to the travelling direction of the paver. In the case of a two-dimensional detection area of the temperature measurement device it is additionally possible to simultaneously detect the temperature values of a plurality of lines at each time of measurement.

According to a further embodiment of the present disclosure, the system or the temperature measurement device comprises units for fixing to the paver or the screed. The detection of the temperature values by means of the temperature measurement device is carried out continuously, at periodic intervals or depending on a speed of the laying process or of the paver. These features allow a simple determination of the position of the measuring points and of the time intervals between the measurements.

According to a further embodiment of the present disclosure, the temperature values are measured at a plurality of specific measuring points at each of the at least two different moments in time. A simultaneous detection of the temperature values for a plurality of known measuring points is advantageous insofar as the cooling behavior of the laid pavement can be ascertained on the basis of an averaging of the detected temperature values of this plurality of measuring points. Thus, it is possible to reduce the influence of incorrect measurements or of punctual material or laying faults on the determination of the cooling behavior. Possible formations of an average value according to an embodiment comprise an arithmetic average, a median, a quadratic mean and/or a weighted arithmetic average for the detected temperature values of the plurality of measuring points.

According to another embodiment of the present disclosure, the evaluation unit is configured for determining the cooling behavior of the laid pavement on the basis of a predetermined mathematical model. Such a mathematical model may take into account at least one additional parameter, such as the base temperature, the thickness of the pavement, the temperature of the ambient air, air moisture, cloud cover, wind speed and/or a further pavement material property, such as the composition of the asphalt.

According to a further embodiment of the disclosure, the evaluation unit is additionally configured for determining a control factor of the laying process of the pavement. This control factor may comprise a speed of a machine of the laying process, a start or stop signal for a machine of the laying process and/or a conveyor belt speed of the laying process. Thus the laying process can be adapted more effectively to the actual temperature, since the cooling behavior of the pavement ascertained from direct measurements is used as a basis. The quality of the laid pavement is therefore improved, since the speed of the laying process can be adapted to the actual laying temperature in an improved manner.

The temperature measurement device according to an embodiment of the present disclosure comprises an infrared camera, an infrared scanner, a pivotable pyrometer, a pyrometer array and/or a line scan camera.

In addition, a paver comprising a system or a temperature measurement device is provided according to a further embodiment of the present disclosure. The temperature measurement device is here integrated in a thermographic module in an advantageous manner. In addition, the evaluation unit may be integrated in the thermographic module. Alternatively, an external evaluation unit is provided. According to a further embodiment of the present disclosure, there is also provided a system or a thermographic module, which is implemented independently of or separately from the paver. According to a further embodiment of the present disclosure, such a system or thermographic module is configured as a mobile device.

Furthermore, the present disclosure relates to a corresponding method for determining the cooling behavior as well as to a computer-readable storage medium with computer-executable instructions, which, when executed, carry out a control method of the type in question.

Embodiments according to the present disclosure will be described below making reference to the attached drawings.

BRIEF DESCRIPTION OF THE DRAWINGS

FIG. 3 shows a two-dimensional temperature profile of the laid pavement, which has been combined line-by-line;

FIGS. 4A, 4B and 4C show different two-dimensional areas for detecting temperature values by means of a temperature measurement device at different moments in time according to an embodiment of the present disclosure;

DETAILED DESCRIPTION

As required, detailed embodiments are disclosed herein; however, it is to be understood that the disclosed embodiments are merely exemplary and that various and alternative forms are possible. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present disclosure.

Figure 1:
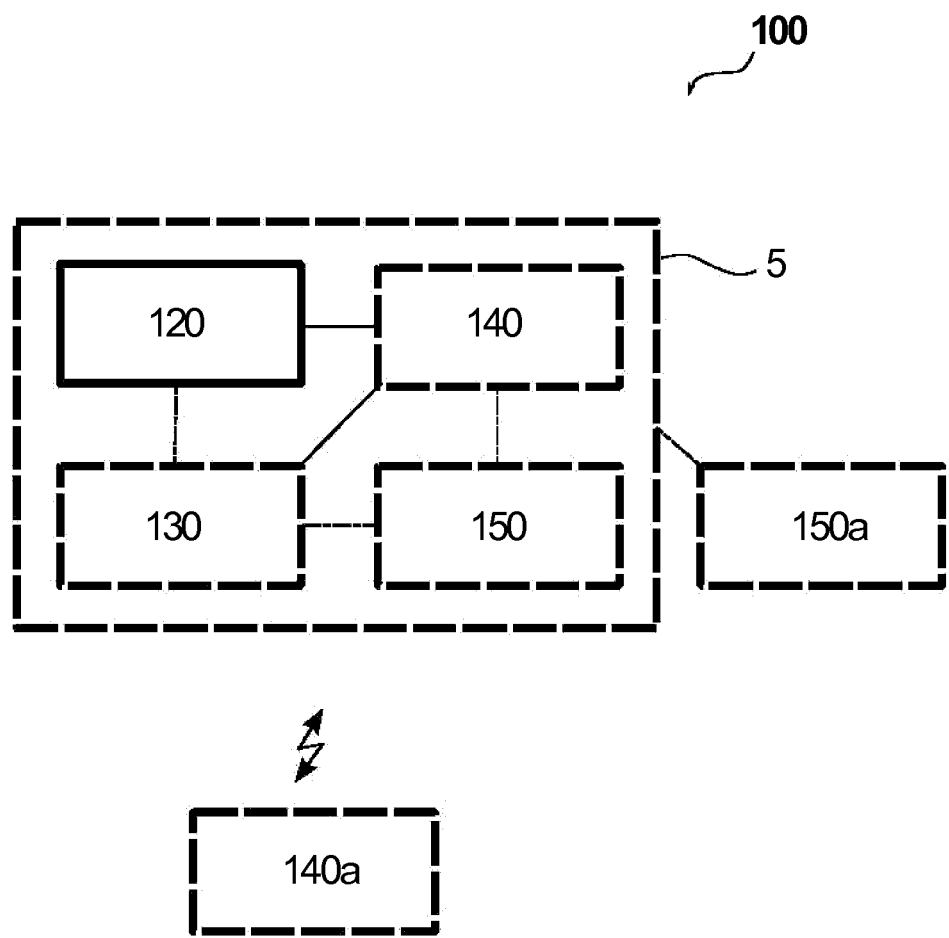
FIG. 1 shows a system including a temperature measurement device according to an embodiment of the present disclosure.

FIG. 1 shows a system 100 according to an embodiment of the present disclosure, which comprises a temperature measurement device 120 and an evaluation unit 140, the evaluation unit 140 and the temperature measurement device 120 communicating with one another for the purpose of data transmission. According to an embodiment, the temperature measurement device 120 and the evaluation unit 140 are integrated in a thermographic module 5.

According to another embodiment, an evaluation unit 140a is arranged outside of or separately from the thermographic module 5 and thus especially remote from the temperature measurement device 120. For this purpose, the evaluation unit 140a can exchange data with the thermographic module 5 by means of a wired or wireless communication link. In the case of an external evaluation unit 140a, both the thermographic module 5 and the evaluation unit 140a may comprise an interface module (not shown), which provides communication and the exchange of data by means of a known communication standard. Preferably, known communications standards are used for this purpose, such as Bluetooth, WLAN according to one of the standards IEEE 802.11x (also referred to as Wi-Fi) or LAN according to one of the standards IEEE 802.3x (also referred to as Ethernet). However, other communication links, such as a mobile radio connection, may be used as well. An external evaluation unit 140a has the advantage that the thermographic module 5 does not require any processing capacities and memory resources for the calculations of the evaluation unit. Moreover, a smart phone, a PC, a laptop, a tablet device or a similar multifunction device may be used as an external evaluation unit 140a. In this case, a suitable control and/or evaluation software, such as a user program or an app, may be deployed or installed on the external device 140a.

Alternatively, the internal evaluation unit 140 or the external evaluation unit 140a is only used as an interface or gateway to a server connected thereto or to a cloud service connected thereto. The server or the cloud service provides in this case the control and/or evaluation functionality of the evaluation unit according to the present disclosure. The here described control and/or evaluation functionality of the evaluation unit according to the present disclosure may also be distributed to the evaluation unit 140, 140a and a server or cloud service connected thereto and/or the temperature measurement device 120.

The temperature measurement device 120 preferably comprises an infrared camera (which is also referred to as thermal imaging camera, thermographic camera or thermal imager), said infrared camera being capable of operating in a line-by-line scan mode. Normally, infrared cameras or line scan cameras provide the possibility of measuring entire lines in a substantially rectangular detection area of the camera. Such a camera allows individual lines to be selected so as to output the respective measured temperature values of this one line or of several selected lines from the camera. For continuous temperature detection of a laid pavement, line-by-line scanning of the laid pavement will be of advantage. For documenting the laying process, the continuously detected surface temperature values may be recorded. To this end, the thermographic module 5 or the evaluation unit 140, 140a may comprise a storage module (not shown). Alternatively or additionally, the acquired data may be transmitted in a suitable form to a connected server or cloud service for the purpose of storage, for further processing or for documentation.

According to another embodiment of the present disclosure, an infrared scanner or thermal scanner, a pivotable pyrometer or a pyrometer array comprising a plurality of pyrometers are provided. They may be provided instead of the infrared camera 120 as well as in addition thereto, as shown by the optional, additional sensor device 130 in FIG. 1. In the case of a plurality of temperature measurement devices 120 and 130, the detected temperature values according to the described embodiments of the disclosure will refer to the respective detected temperature values of these temperature measurement devices, even if this should not be explicitly mentioned. According to another embodiment of the disclosure, the optional sensor device 130 is an additional sensor for measuring the base temperature and/or the ambient temperature.

It will be of advantage to configure the evaluation unit 140 and/or 140a such that a cooling behavior of the laid pavement 3 is determined on the basis of temperature values detected by the temperature measurement device 120. The determination takes place during laying and allows the ascertained cooling behavior to be taken into account in the control of the laying process. Due to the importance of the laying temperature of the pavement during the laying process, in particular as regards the compacting of the layers by the machines (rollers) following the paver 1, the laying process carried out by means of the individual machines of the paving train is preferably adapted to the laying temperature. For this purpose, there are mathematical models or look-up tables for determining a suitable control factor of the laying process from previously ascertained or inputted parameters. These parameters to be inputted or measured are e.g., the base temperature, the thickness of the pavement, the temperature of the ambient air, air moisture, cloud cover, wind speed and/or other pavement material properties, such as the composition of the asphalt. These environmental and weather factors essentially serve to estimate the cooling behavior, so as to approach the actual processing temperature during laying in the best possible way and optimize the laying process through appropriate deceleration or acceleration of the machines taking part in the process. The ascertained control factors of the laying process may comprise the speed of a machine of the laying process, a start or stop signal for a machine of the laying process or a conveyor belt speed of the laying process. These control factors can be redefined or adapted in a suitable way.

Making use of the direct determination of the cooling behavior of the pavement 3 according to the present disclosure, the number of manual inputs required and the additional measurement of environmental and weather parameters is either reduced or said inputs and measurements are rendered completely superfluous. Likewise, the disclosure thus allows to dispense with the respective additional sensors for measuring the environmental and weather parameters. This facilitates handling during the laying process, leads to less complex and consequently less error-prone systems and results in an improvement of the control and monitoring of the laying process. According to an alternative provided by a further embodiment of the present disclosure, the cooling behavior ascertained from direct measurements is used, in addition to environmental and weather parameters, for determining the temperature profile and for the subsequent control of the laying process. This embodiment improves the accuracy of control and monitoring of the laying process still further.

Figure 2:
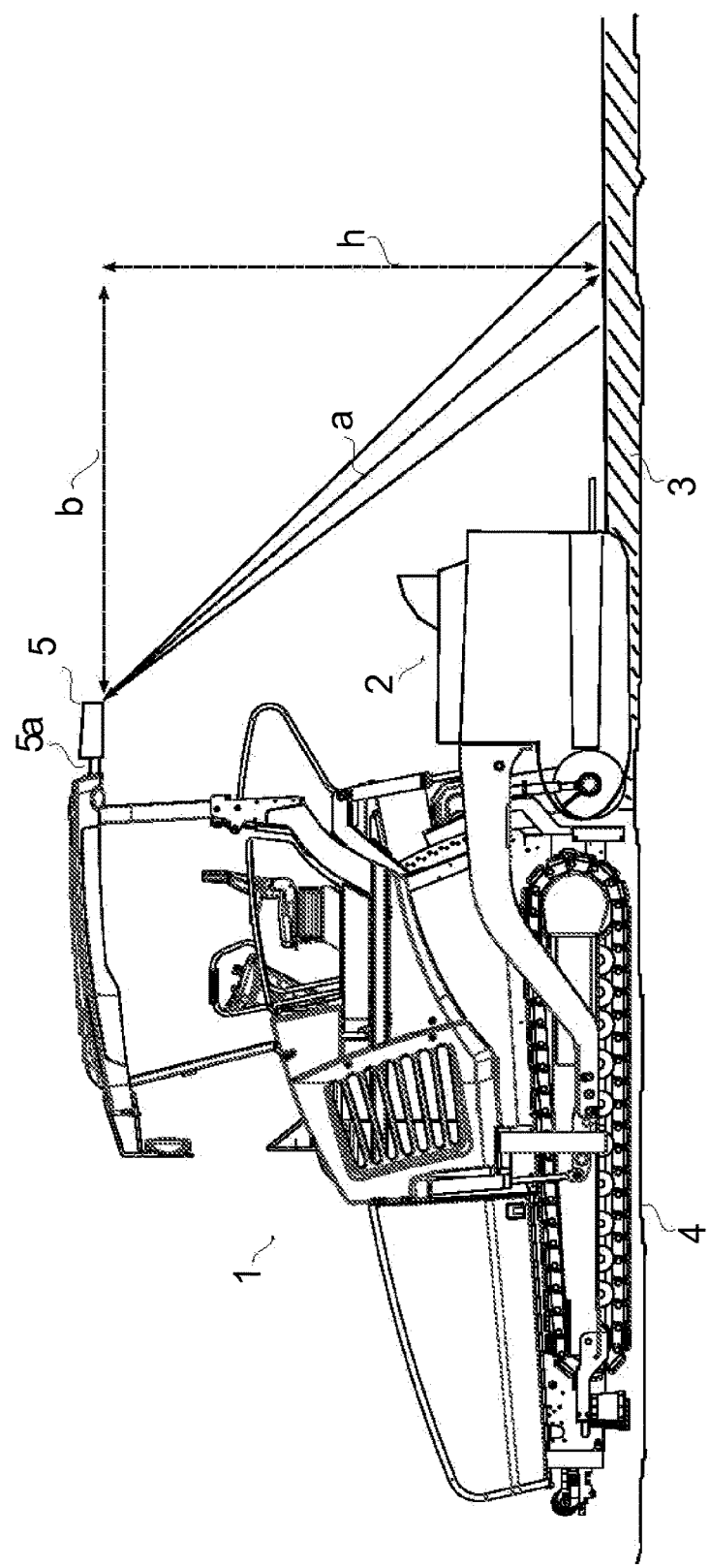
FIG. 2 shows a paver for detecting the laying temperature of the pavement during the laying process according to an embodiment of the present disclosure.

FIG. 2 shows exemplarily a paver 1 on a planum 4 during laying of a pavement 3, e.g., asphalt, by means of a screed 2 drawn by the paver 1. In the embodiment shown, the roof of the paver 1 has attached thereto a thermographic module 5 by means of fixing units 5a. The thermographic module 5, which comprises at least the temperature measurement device 120 of the system 100 according to FIG. 1, is positioned on a level h above the pavement 3 and is configured to detect the temperature of an area of the laid pavement 3 at a distance b behind the thermographic module 5, i.e., corresponding to the height h, at a distance a from the thermographic module 5. Temperature detection may preferably be carried out line by line in a direction transversal to the travelling direction 300 of the paver 1 along the width of the laid pavement 3. Thus, the exact location or the exact measuring point on the pavement 3 can be ascertained or determined for each temperature measurement of the temperature measurement device 120. Alternatively, the thermographic module 5 or a temperature measurement device 120, 130 of the system 100 can be attached to the screed.

Since the distance in time between the measurements as well as the distance in space between the measurements are therefore known or can be ascertained, the detected temperature data can be used for representing the temperature over time and for ascertaining thus also a measure for the cooling or the cooling rate of the pavement surface.

According to an embodiment, an overall record of comparatively large areas of the laid pavement 3 is additionally established at predetermined time intervals during temperature detection. This is preferably done by making use of a temperature measurement device 120 for line-by-line scanning of the laid pavement behind the paver 1 or after precompacting through the screed 2. FIG. 3 shows exemplarily such an overall record 340 representing the temperature profile of the laid pavement 3, which has been established by combining or condensing individual scanned lines 311, 321, 331 to an areal, two-dimensional temperature profile or a so-called temperature map. The surface temperatures of the laid pavement detected by means of the temperature measurement device 120 are here shown, and it is in particular possible to discern the temperature differences between the different locations or measuring points of the pavement 3. In FIGS. 3 and 4A to 4C, the travelling direction 300 of the paver 1 is from the right to the left, so that e.g., line 311 was detected earlier than line 321. Such an overall record of the two-dimensional temperature profile may be stored for the purpose of documentation or transmitted to a server or a cloud service.

Figure 4A:
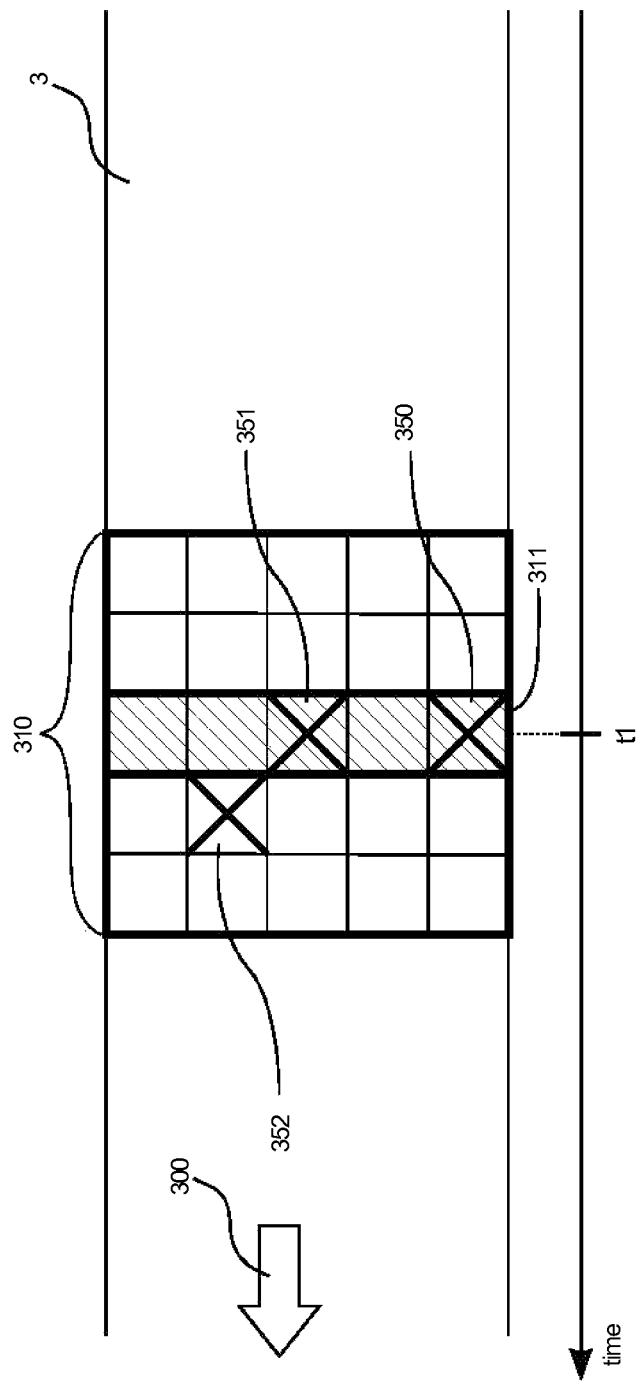
Figure 4B:
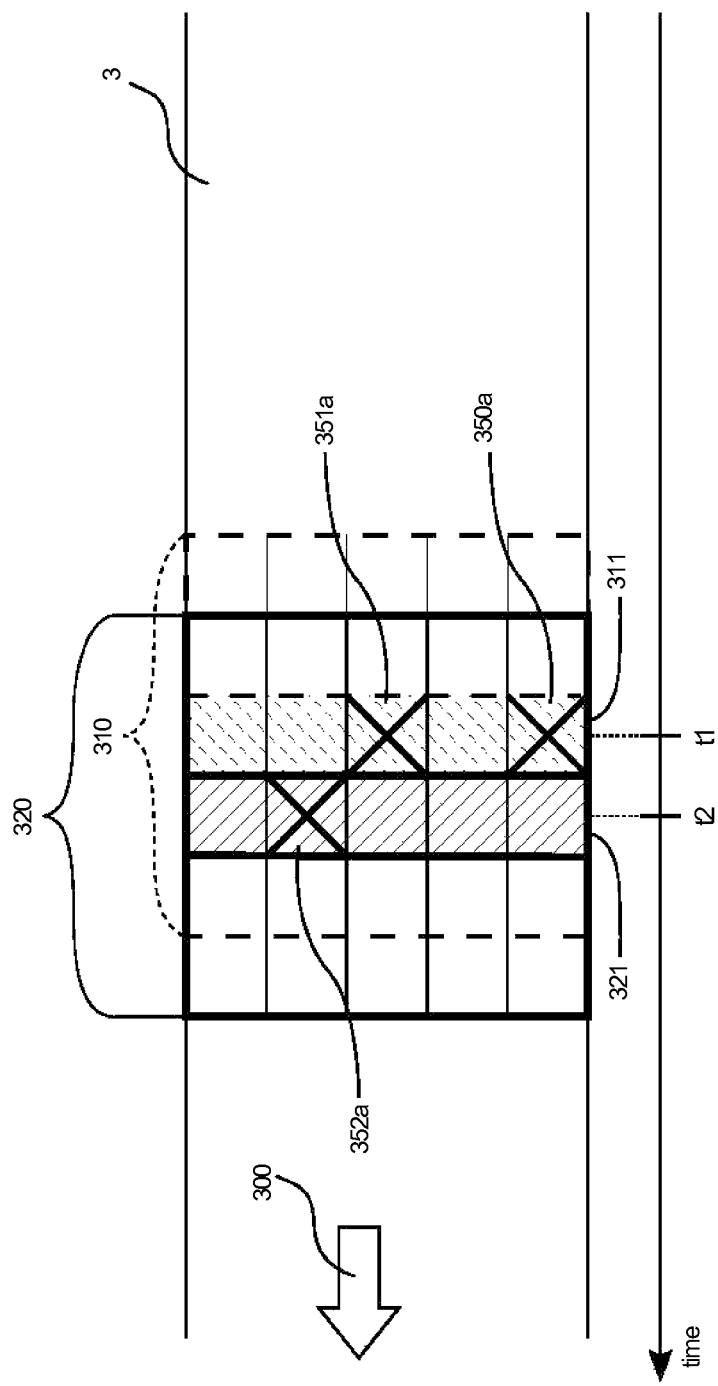

The respective FIGS. 4A to 4C show the detected temperature data of the pavement 3 at different moments in time during the laying process or during detection through the thermographic module 5 and its temperature measurement device 120. The two-dimensional area 310 shown in FIG. 4A was detected by the temperature measurement device 120 during a measurement at a moment in time t1. The area 310 shows exemplarily five scanned lines comprising each five measuring points or locations at the surface of the pavement 3. The number of lines and measuring points may, however, vary and depends especially on the infrared or line scan camera used. According to another embodiment of the disclosure, only a two-dimensional temperature profile 310 is detected, without explicit lines being provided. As shown in FIG. 4A, the line or the two-dimensional detection area 310 of the temperature measurement device 120 may cover the entire width of the pavement 3. According to a further embodiment of the disclosure, this is, however, not demanded, so that the detection area 310 of the temperature measurement device 120 may only cover part of the entire width of the pavement 3. Especially the margins of the pavement 3 may here not be included.

The temperature measurement according to the example of FIG. 4A takes place at the moment in time t1. According to an embodiment of the disclosure, temperature values of a line 311 are detected at the moment in time t1. This is done e.g., for establishing the above mentioned temperature map of the pavement. Exemplarily, three specific measuring points 350, 351 and 352 are highlighted in FIG. 4A, the measuring points 350 and 351 lying in said line 311, whereas measuring point 352 lies outside said line 311. In a corresponding manner, one or a plurality of measuring points 350, 351, 352 can be identified in a detected two-dimensional temperature profile 310 without explicit line rastering. Since the position and/or the orientation of the thermographic module 5 or of the temperature measurement device 120, 130 are known, the exact position of the measuring points 350, 351, 352 on the pavement 3 can either be predetermined or ascertained. In the first case, the evaluation unit 140 can predetermine the exact position of the measuring points that are subsequently used by the temperature measurement device 120, 130 for the purpose of measurement. In the case of an external evaluation unit 140a, the measuring points predetermined by the evaluation unit can be transmitted to the thermographic module 5.

FIG. 4B shows, in accordance with the example of FIG. 4A, the temperature measurement by means of the temperature measurement device 120 at the second moment in time t2 during laying, said second moment in time t2 coming after said moment in time t1. According to an embodiment of the disclosure providing line-by-line scanning, the moment in time t2 concerns the detection of a second line 321 within the detection area 320 of the temperature measurement device 120. In comparison with the detection area 310 at the moment in time t1, the two-dimensional detection area 320, which is detected by the temperature measurement device 120 at the moment in time t2, migrated further to the left in accordance with the travelling direction 300 of the paver 1. The measuring points highlighted in FIG. 4B are again the three specific measuring points 350, 351 and 352 according to FIG. 4A, which, however, now migrate to the right in a direction opposite to the travelling direction 300 of the paver. For better discrimination, the three specific measuring points in FIG. 4B are designated with 350a, 351a and 352a, so as to illustrate that, on the one hand, these measuring points are located at the same absolute positions of the pavement 3 as in FIG. 4A at the moment in time t1. On the other hand, temperature detection at these specific measuring points or absolute positions takes place at a second moment in time t2 and concerns a second measurement process. For further illustration, the first measuring process executed at the moment in time t1 and the corresponding detection area 310 as well as line 311 of the latter are additionally shown by a broken line in FIG. 4B.

In a manner corresponding to that which is shown in FIG. 4B, FIG. 4C shows a third measuring process at the moment in time t3 coming after a moment in time t2. This figure shows the two-dimensional detection area 330 and its ascertained temperature profile line 331 at a moment in time t3. In comparison with the detection areas 310 and 320 at the moments in time t1 and t2, the three highlighted measuring points 350b, 351b and 352b migrate at the moment in time t3 in the detection area 330 further to the right in a direction opposite to the travelling direction 300, since the paver 1 and, together therewith, the thermographic module 5 or the temperature measurement device 120 move further to the left in the travelling direction 300.

Figure 5:
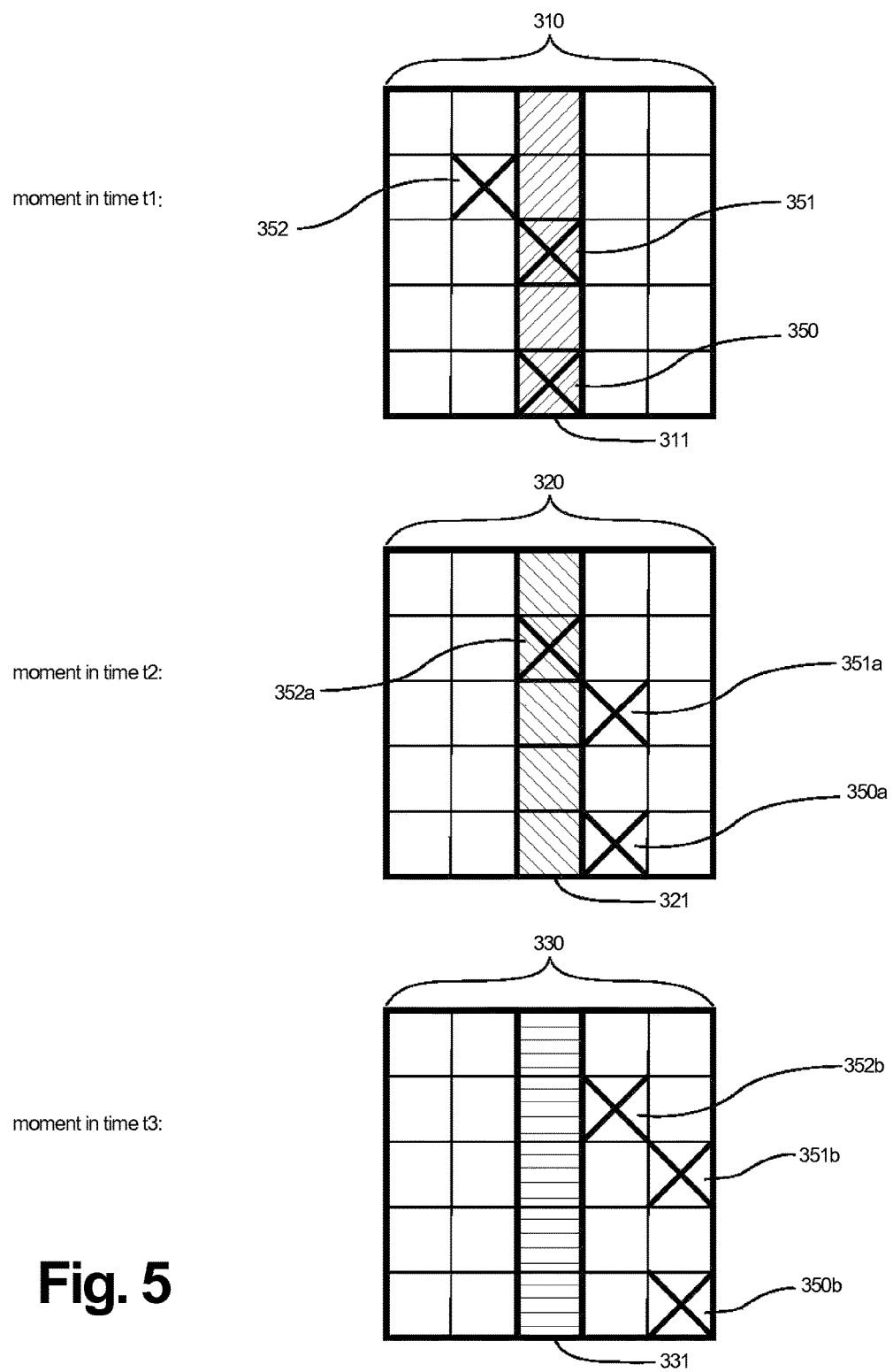
FIG. 5 shows different two-dimensional detection areas of FIGS. 4A, 4B and 4C.

Hence, the individual measuring points on the laid pavement 3 undergo a plurality of recordings on the part of the temperature measurement device 120, which are made at different, successive moments in time. The three recordings 310, 320, 330 at the moments in time t1, t2 and t3 according to the example of FIGS. 4A to 4C are separately compared with one another in FIG. 5 once more. These different temperature measurements for one and the same measuring point on the pavement 3, e.g., for the measuring point 351, 351a, 351b, can be used for determining therefrom an actual cooling behavior of the laid pavement 3. To this end, the time intervals be-tween the different temperature measurements at the moments in time t1, t2 and t3 are used. These time intervals may be specified in advance, e.g., as periodic intervals, which means that the evaluation unit 140, 140a knows the time intervals between the measurements. According to an alternative provided by another embodiment, the time intervals of the measurements can be adapted to the laying process, in particular to the speed with which the pavement to be detected is laid. In this case, the time intervals or the absolute measuring times can be made known to the evaluation unit 140, 140a.

According to an embodiment of the present disclosure, a specific measuring point, e.g., the location 351, is predetermined or specified for each measurement in accordance with the actual movement of the temperature measurement device 120 in the travelling direction 300. In this respect, the evaluation unit 140, 140a can determine or specify the specific measuring point or points and make it/them known to the temperature measurement device 120, 130 or the thermographic module 5. Alternatively, the specific measuring point on the pavement, e.g., the location 351, can be ascertained subsequently from the measured two-dimensional detection data 310, 320 and 330 on the basis of the known position of the temperature measurement device 120, 130 relative to the paver 1 and the screed 2. As a further alternative, the position of the temperature measurement device 120, 130 relative to the paver 1 and the screed 2 is specified and is therefore an invariable, known quantity. Determining or specifying the position of a specific measuring point is thus possible at any moment in time, since, as has been described hereinbefore, the distance to the paver 1 or the screed 2 is either specified, or has been predetermined by the evaluation unit, or can be ascertained for the measurement results on the basis of the known position and/or adjustment of the temperature measuring device during the measuring process.

According to a further embodiment of the present disclosure, the determination of the cooling behavior of the laid pavement 3 is based not only on temperature measurements at a respective specific measuring point 351, 351a, 351b, but a plurality of measuring points can be considered simultaneously in the case of each temperature measurement, e.g., the measuring points 350, 351 and 352 at the moment in time t1. Exemplarily, all the measuring points within one line or different measuring points in different lines can be taken into consideration. In this respect, the plurality of measuring points can, according to an embodiment of the disclosure, be combined by means of a mathematical model such that possible incorrect measurements or other outliers in the temperature measurement values will be compensated for, filtered out, or will at least remain without substantial influence on the determination of the cooling behavior and a respective control of the laying process based on said cooling behavior. According to a simple model, one or a plurality of measuring points lying, by a predetermined amount, above or below an arithmetic average of all measuring points is/are not taken into account in the determination of the cooling behavior. Hence, isolated deviations, which are based either on incorrect measurements or on irregularities of the laying material, e.g., inclusions, are left out of account. Alternatively or additionally, the ascertained cooling behavior may, according to a further embodiment of the invention, be based on averaging of the simultaneously detected temperature data of a plurality of measuring points. The averaging may comprise e.g., an arithmetic average, a median, a quadratic mean and/or a weighted arithmetic average for the temperature values of the plurality of simultaneously detected measuring points.

Figure 6:
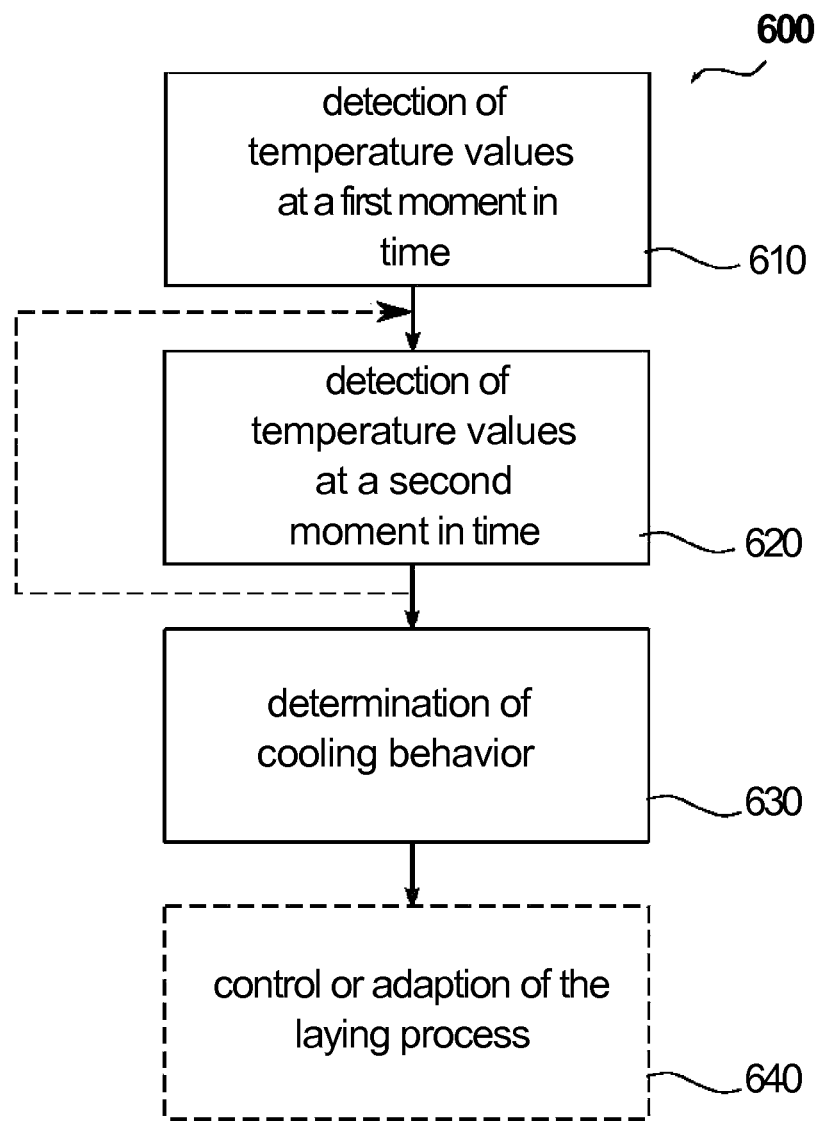
FIG. 6 shows a method for repeatedly detecting temperature values and for determining a cooling behavior according to an embodiment of the present disclosure.

FIG. 6 shows schematically the steps of a method according to an embodiment of the present disclosure used for repeatedly detecting temperature values and for determining a cooling behavior of the pavement 3 laid by a paver 1 or a road finisher. The method can be executed by the above described system 100. In step 610, the temperature of one or of a plurality of specific measuring points 351, 351a, 351b is detected by the temperature measurement device 120, 130 at a first moment in time (t1) during the laying process of the pavement. As described above, the specific measuring point or points lie in the area of the laid pavement 3, which is detected by the temperature measurement device 120, 130, and are either specified, predetermined or ascertainable. In a subsequent step 620, temperature values for the measuring point or points are again detected by the temperature measurement device 120, 130 at a second moment in time due to the fact that the measuring point or points lie within the detection area 320 of the temperature measurement device 120, 130 at said second moment in time. Step 620 can be repeated several times, so that additional temperature values for the measuring point or points can be detected at additional moments in time. The detected temperature values for the specific measuring point or points at the at least two different moments in time are then used by the evaluation unit 140, 140a in a step 630 for determining the cooling behavior of the laid pavement 3. In addition, the thus ascertained cooling behavior can be outputted, stored or displayed according to a further embodiment of the present disclosure. For the purpose of display, a screen may be provided on the paver 1 or at a location remote from the paver, said screen being connected to the evaluation unit 140, 140a or the system 100. For the purpose of storage or documentation, the data can be stored in a memory of the evaluation unit 140, 140a or of the system 100. Likewise, the data may be transmitted to a remote server or a cloud service.

According to an embodiment of the present disclosure, the thus ascertained cooling behavior is then used in a further step 640, e.g., for adapting or controlling the laying process. Step 640 need not be executed by the system 100 and is optional for said system 100 according to the present disclosure. The method according to FIG. 6 may then start from the beginning or may continuously be executed during the laying process or the movement of the paver 1.

Figure 7:
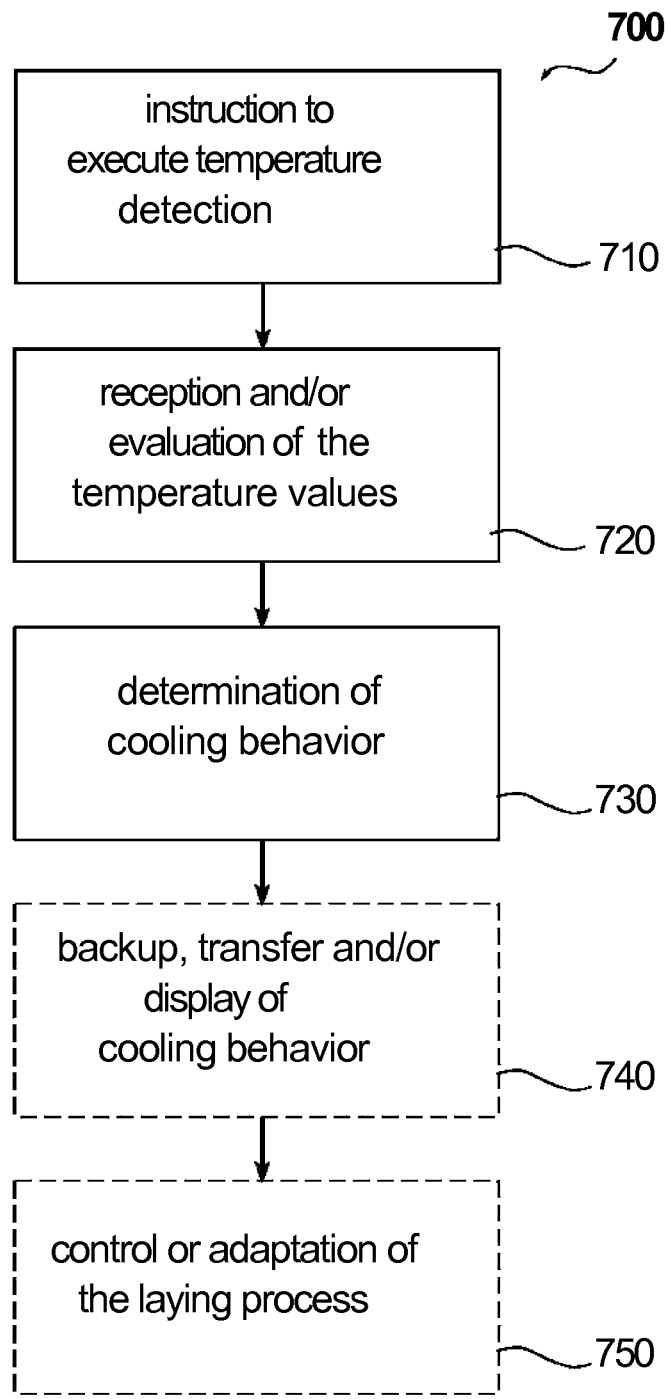
FIG. 7 shows a control method according to an embodiment of the present disclosure, which is carried out when instructions of a computer-readable storage medium are executed.

FIG. 7 shows steps of a corresponding control method 700 according to a further embodiment of the present disclosure, which is carried out when computer-executable instructions of a computer-readable storage medium are executed. For the purpose of execution, the evaluation unit 140 or 140a may be used or a control device communicating with the evaluation unit 140, 140a by means of a suitable interface for data transmission. The computer-aided execution of the computer-executable instructions can be carried out through a control device of the system 100 within the thermographic module 5, on the paver 1 or at a location remote from the paver 1. In step 710 of the control method 700, a temperature measurement device 120, 130 or a thermographic module 5 is instructed to detect, during the laying process, the temperature of the pavement 3 laid by a paver 1, as described above. Step 710 may comprise the instruction for the temperature measurement device 120, 130 and the necessary parameters therefor. According to a further embodiment of the disclosure, step 710 additionally comprises one or a plurality of instructions and/or the necessary parameters therefor for the temperature measurement device 120, 130 for a plurality of measurements at the at least two different moments in time (t1, t2, t3). Alternatively, the measurements at the at least two different moments in time (t1, t2, t3) may be separate steps of the control method 700.

In step 720, the temperature values, which were detected by the temperature measurement device 120, 130 during the laying process, are received or evaluated. If necessary, step 720 comprises, according to an embodiment of the disclosure, the reception or evaluation of further parameters, such as the time interval between the measurements or the position of the measuring points. In step 730 of the control method, the cooling behavior of the pavement 3 is ascertained in accordance with the above described embodiments. In step 740 of the control method, the ascertained cooling behavior is outputted, stored or transmitted to a connected receiving unit. Step 740 is here optional and concerns only the backup, transfer or display of the ascertained cooling behavior. The thus ascertained cooling behavior may then be used in a further step 750, e.g., for adapting or controlling the laying process. Respective control data or control commands can be transmitted to the respective machines of the laying process in step 750 or in a further step. Steps 740 and 750 are here optional for the present disclosure and concern only an additional embodiment of the disclosure.

The methods 600 and 700 may, in accordance with the above described embodiments of the sys-tem 100 or of the paver 1, be advantageously developed still further. In FIGS. 6 and 7, the optional steps are indicated by a broken line. Accordingly, the method 600 can be realized by the above described system 100 and advantageously developed still further. The method 700 can be realized by the evaluation unit 140, 140a and advantageously developed still further. As a further embodiment of the disclosure, the control method according to FIG. 7 can be realized, instead of the above described evaluation unit 140, 140a. In this embodiment, the evaluation unit 140, 140a is configured as a software program.

While exemplary embodiments are described above, it is not intended that these embodiments describe all possible forms according to the disclosure. The words used in the specification are words of description rather than limitation, and it is understood that various changes may be made without departing from the spirit and scope of the disclosure. Additionally, the features of various implementing embodiments may be combined to form further embodiments according to the disclosure.

What is claimed is:

1. A system comprising:
a temperature measurement device for repeatedly detecting surface temperature values of a pavement laid by a paver during a laying process, wherein the system is configured for determining a surface temperature value for a specific measuring point at at least two different instances in time using the temperature measurement device, the specific measuring point being in an area of the laid pavement; and an evaluation unit configured for determining a cooling behavior of the laid pavement from the at least two surface temperature values determined for the specific measuring point at the at least two different instances in time, wherein the evaluation unit is further configured to determine a control factor of the laying process of the pavement using the determined cooling behavior of the laid pavement, and wherein the control factor is usable for controlling an aspect of the laying process of the pavement.

2. The system according to claim 1 wherein the respective time interval between the at least two different instances in time is predetermined, and wherein the evaluation unit is further configured for determining the cooling behavior of the laid pavement based on the respective time interval between the at least two different instances in time.

3. The system according to claim 1 wherein the system is configured to determine the temperature values during or after pre-compacting by a screed of the paver,
wherein the temperature measurement device is configured for detecting temperature values at measuring points in the area of the laid pavement having each a pre-determined or an ascertainable distance to the paver or the screed, and
wherein the position of the specific measuring point is ascertained on the basis of its respective distance to the paver or the screed at the at least two different instances in time during the laying process.

4. The system according to claim 1 wherein the temperature measurement device is configured to determine the temperature values line-by-line, each determined line representing a temperature profile of the laid pavement transversal to the travel direction of the paver.

5. The system according to claim 1 wherein the temperature measurement device is configured for determining a plurality of temperature values in a two-dimensional area on the surface of the laid pavement at each of the instances in time, and
wherein the at least two different instances in time correspond to at least two different two-dimensional areas, the at least two different two-dimensional areas overlapping and each of the at least two different two-dimensional areas including the specific measuring point.

6. The system according to claim 5 wherein the temperature measurement device is configured to determine the temperature values line-by-line, each determined line representing a temperature profile of the laid pavement transversal to the travel direction of the paver.

7. The system according to claim 6 wherein the temperature measurement device is configured for determining temperature values of a plurality of lines at each instance in time, and wherein the plurality of lines at an instance in time represent one of the two-dimensional areas.

8. The system according to claim 1 wherein the system or the temperature measurement device comprises units for mounting to the paver, and wherein the temperature measurement device is configured to determine the temperature values during the laying process of the pavement, and
wherein the temperature measurement device is configured to determine the temperature values continuously, at periodic intervals or depending on a speed of the laying process or of the paver.

9. The system according to claim 1 wherein the system is configured for determining a respective temperature value for a plurality of specific measuring points at each of the at least two different instances in time, and
wherein the evaluation unit is configured for determining the cooling behavior of the laid pavement based on a predetermined averaging of the temperature values of the plurality of specific measuring points.

10. The system according to claim 9 wherein the predetermined averaging is an arithmetic average, a median, a quadratic mean and/or a weighted arithmetic average for the temperature values of the plurality of specific measuring points.

11. The system according to claim 1 wherein the evaluation unit is configured for determining the cooling behavior of the laid pavement based on a predetermined mathematical model, the mathematical model being further based on at least one additional parameter, the at least one additional parameter comprising a base temperature, a thickness of the pavement, a temperature of ambient air, an air moisture, a cloud cover, a wind speed and/or a pavement material property.

12. The system according to claim 1 wherein the control factor comprises a speed of a machine of the laying process, a start or stop signal for a machine of the laying process and/or a conveyor belt speed of the laying process.

13. The system according to claim 1 wherein the temperature measurement device comprises an infrared camera, an infrared scanner, a pivotable pyrometer, a pyrometer array and/or a line scan camera.

14. A paver comprising a system according to claim 1.

15. A method for determining a cooling behavior of a pavement laid by a paver, the method comprising:
determining by a temperature measurement device a first surface temperature value for a specific measuring point at a first instance in time during a laying process of the pavement, the specific measuring point being in an area of the pavement laid by the paver;
determining by the temperature measurement device at least a second surface temperature value for the specific measuring point at at least a second instance in time during the laying process, the at least second instance in time being after the first instance in time;
determining a cooling behavior of the laid pavement from the at least two determined surface temperature values for the specific measuring point;
determining, using an evaluation unit, a control factor of the laying process of the pavement using the determined cooling behavior of the laid pavement; and
controlling an aspect of the laying process of the pavement based on the control factor.

16. A non-transitory computer-readable storage medium with stored computer-executable instructions, which, when executed, carry out a control method comprising the following steps:
instructing a temperature measurement device to determine a first surface temperature value for a specific measuring point at a first instance in time during a laying process of pavement by a paver, the specific measuring point being in an area of the pavement laid by the paver;
instructing the temperature measurement device to determine at least a second surface temperature value for the specific measuring point at at least a second instance in time during the laying process, the at least second instance in time being after the first instance in time;

determining a cooling behavior of the laid pavement from the at least two determined surface temperature values for the specific measuring point;

determining a control factor of the laying process of the pavement using the determined cooling behavior of the laid pavement; and controlling an aspect of the laying process of the pavement based on the control factor.

17. The computer-readable storage medium of claim 16 wherein the computer-executable instructions are configured to carry out the determining step at an evaluation unit that is configured to receive the at least two determined temperature values.

18. The method according to claim 15 wherein the control factor comprises a speed of a machine of the laying process, a start or stop signal for a machine of the laying process and/or a conveyor belt speed of the laying process.

19. The computer-readable storage medium of claim 16 wherein the control factor comprises a speed of a machine of the laying process, a start or stop signal for a machine of the laying process and/or a conveyor belt speed of the laying process.

* * * * *